United States Patent
Gillis et al.

(10) Patent No.: US 12,064,733 B2
(45) Date of Patent: Aug. 20, 2024

(54) STATIC MIXING DEVICE AND METHOD FOR MIXING PHOSGENE AND AN ORGANIC AMINE

(71) Applicant: Dow Global Technologies LLC, Midland, MI (US)

(72) Inventors: Paul A. Gillis, Lake Jackson, TX (US); Quan Yuan, Sugarland, TX (US)

(73) Assignee: Dow Global Technologies LLC, Midland, MI (US)

( * ) Notice: Subject to any disclaimer, the term of this patent is extended or adjusted under 35 U.S.C. 154(b) by 785 days.

(21) Appl. No.: 17/257,083

(22) PCT Filed: Jul. 3, 2019

(86) PCT No.: PCT/US2019/040554
§ 371 (c)(1),
(2) Date: Dec. 30, 2020

(87) PCT Pub. No.: WO2020/027977
PCT Pub. Date: Feb. 6, 2020

(65) Prior Publication Data
US 2021/0138411 A1    May 13, 2021

Related U.S. Application Data

(60) Provisional application No. 62/711,652, filed on Jul. 30, 2018.

(51) Int. Cl.
*B01F 25/314* (2022.01)
*B01F 25/433* (2022.01)
*B01J 19/24* (2006.01)
*B01J 19/26* (2006.01)
*C07C 263/10* (2006.01)

(52) U.S. Cl.
CPC .... *B01F 25/3141* (2022.01); *B01F 25/31423* (2022.01); *B01F 25/4336* (2022.01); *B01J 19/2405* (2013.01); *B01J 19/26* (2013.01); *C07C 263/10* (2013.01)

(58) Field of Classification Search
CPC .......... B01F 25/3141; B01F 25/31423; B07C 263/10
USPC ...................................... 366/167.1
See application file for complete search history.

(56) References Cited

U.S. PATENT DOCUMENTS

| | | | |
|---|---|---|---|
| 5,931,579 A * | 8/1999 | Gallus | B01J 19/1887 366/178.2 |
| 8,173,833 B2 | 5/2012 | Woelfert | |
| 8,829,232 B2 | 9/2014 | Penzel | |
| 2010/0137634 A1 * | 6/2010 | Ding | B01J 4/002 422/236 |
| 2010/0305356 A1 * | 12/2010 | Olbert | C07C 263/10 366/177.1 |
| 2011/0230679 A1 * | 9/2011 | Gillis | B01F 25/4336 564/305 |

* cited by examiner

*Primary Examiner* — Marc C Howell

(57) ABSTRACT

Phosgene is mixed with an organic polyamine to produce polyisocyanate compounds. A phosgene flow is established in a conduit (15), and the organic polyamine is injected into the phosgene flow. A constricted region (4) of the conduit (15) resides downstream of the point of the polyamine injection. The presence of the constricted region (4) reduces by-product formation.

4 Claims, 2 Drawing Sheets

STATIC MIXING DEVICE AND METHOD FOR MIXING PHOSGENE AND AN ORGANIC AMINE

The present invention relates to a method for mixing phosgene with an organic amine and to a static mixing device useful in the method.

Polyisocyanates are made industrially by the reaction of phosgene with polyamine compounds. In large-scale industrial processes, the organic polyamine typically is injected continuously into a flowing phosgene stream. The phosgene is usually in excess. The reaction is fast and highly exothermic and produces HCl as a by-product. Rapid and thorough mixing is needed to take advantage of consuming the polyamine in certain fast reactions.

This process is susceptible to the formation of unwanted by-products. These can include, for example, various urea, carbodiimide, uretonimine and other materials. These often form at least partially as a result of incomplete mixing of the organic polyamine and the phosgene. They often form in very low concentration but build up over time and foul process equipment.

For that reason, much effort has gone into designing mixing devices for these phosgenation reactions. Because of the rather severe reaction conditions (presence of phosgene and hydrogen chloride, elevated temperature and pressure, for example), static mixing devices are generally favored. Examples of such static mixing devices are described, for example, in U.S. Pat. Nos. 8,829,232, 8,173,833, US Published Patent Application No. 2011/0230679 and US Published Patent Application No. 2013/0176814.

The phosgenation mixer in US Published Patent Application No. 2011-0230679 describes the use of a "guide element" that is disposed with the mixer body. The guide element occupies the center of an otherwise tubular conduit, converting a circular phosgene flow path into an annular one as the phosgene passes by the guide element. The organic polyamine is introduced through multiple jets that are located in the section where the annular phosgene flow path exists. This promotes high mixer performance. Despite the improvements offered by this mixer design, it is desirable to reduce by-product formation even more.

This invention is in one aspect a method for mixing phosgene with an organic polyamine comprising;

establishing an axially-directed phosgene flow through a conduit having an outer sidewall;

injecting the organic polyamine into the conduit through multiple circumferentially aligned jets, each such jet having a hydrodynamic diameter $D_j$ and each having a location on a wall of the conduit, to establish multiple organic polyamine streams into the axially directed phosgene flow; wherein the conduit has a cross-sectional area A at the axial location of the one or more jets;

then passing the phosgene and the organic polyamine through a constricted region of the conduit that has a cross-sectional area less than A, wherein the constricted has a smallest cross-sectional area that is 50 to 95% of cross-sectional area A and wherein the constricted region begins downstream of the multiple jets at a distance equal to 0.01 to 3 times the diameter hydrodynamic $D_j$ and extends downstream of the multiple jets to a distance that is no greater than 50 times the hydrodynamic diameter $D_j$; and thereafter passing the phosgene and the organic polyamine into a region having a cross-sectional area at least as large as cross-sectional area A.

The invention is also a static mixing device comprising:

a) a conduit defined by an outer sidewall and optionally an inner sidewall, the conduit having a longitudinal axis, an inlet end for introducing a first fluid and an outlet end for removing a reaction product stream, the conduit defining a fluid flow path;

b) a plurality of circumferentially-aligned jets each having a location on a sidewall of the conduit between said inlet and outlet ends of the conduit, each jet providing a fluid flow path through the outer sidewall and into the conduit and each such jet having a hydrodynamic diameter $D_j$; wherein the conduit has a cross-sectional area A at the location of the jets;

c) a constricted region of the conduit, the constricted region characterized in having a cross-sectional area less than A and being located downstream of the circumferentially-aligned jets and upstream of the outlet end of the conduit, wherein the constricted region has a smallest cross-sectional area that is 50 to 95% of cross-sectional area A and the constricted region begins downstream of the multiple jets at a distance equal to 0.01 to 3 times the hydrodynamic diameter $D_j$ and extends downstream of the jets to a distance that is no greater than 50 times the hydrodynamic diameter $D_j$; and d) a region, downstream of and in fluid communication with the constricted region of the conduit, which has a cross-sectional area of at least A.

Figure 1:
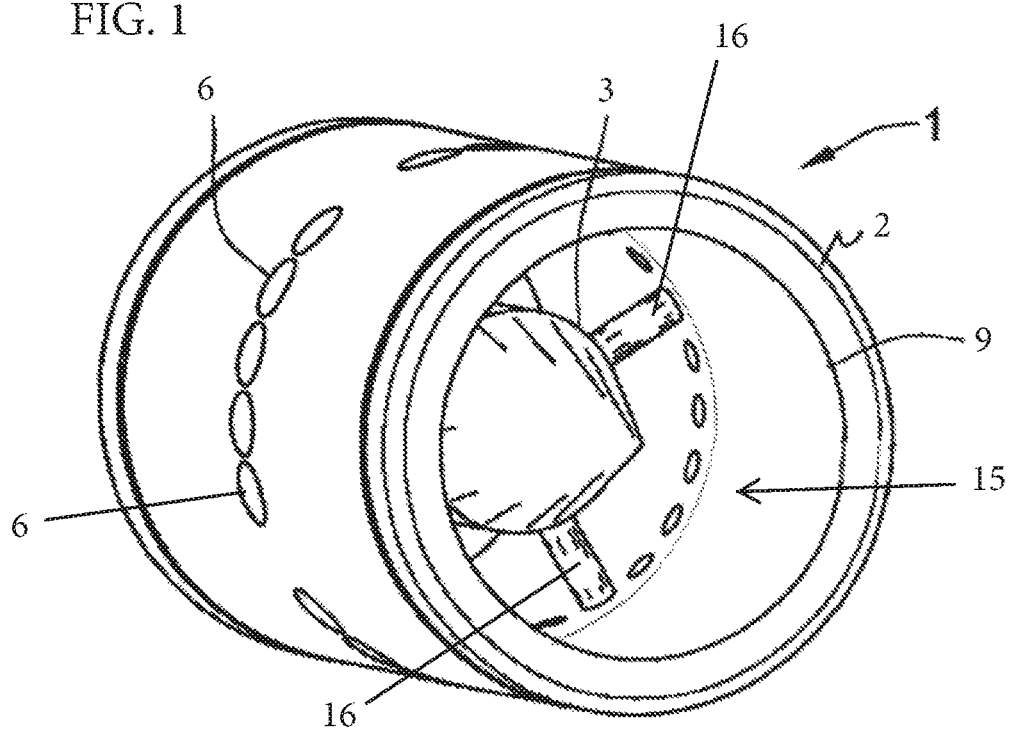
FIG. 1 is a perspective view of an embodiment of a static mixing device of the invention.
Figure 2:
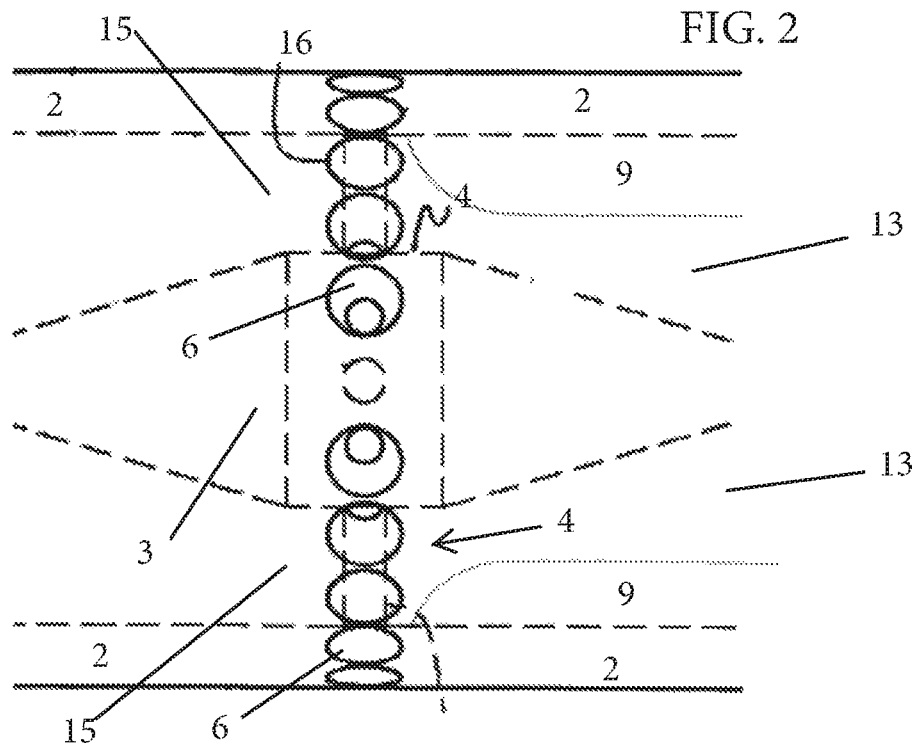
FIG. 2 is a side sectional view of an embodiment of a static mixing device of the invention.
Figure 3:
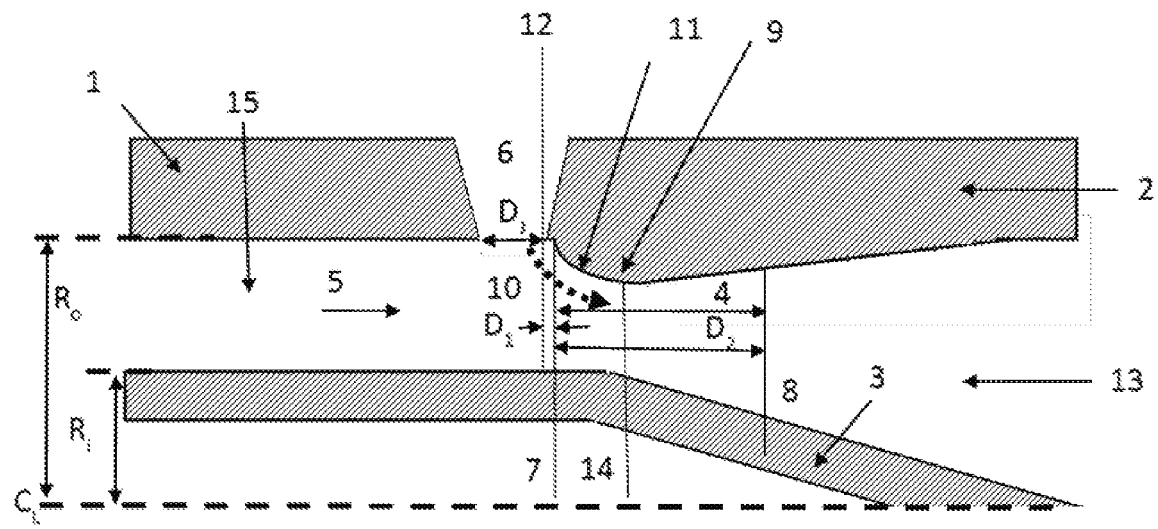
FIG. 3 is an enlarged sectional view showing details of the static mixing device of FIG. 2.

Turning to FIGS. 1-3, phosgenation mixer 1 includes outer sidewall 2 and central insert 3, which together define conduit 15 through which an axially directed flow of phosgene is established, upstream of jets 6, in the direction indicated by arrow 5 (FIG. 3). A plurality of circumferentially-aligned jets 6 penetrate outer sidewall 2, each jet 6 forming a flow path for injecting an organic polyamine stream from the outside of outer sidewall 2 into conduit 15. Supports 16 hold central insert 3 in place within phosgenation mixer 1. Central insert 3 preferably is centrally aligned along the central axis of phosgenation mixer 1 such that the width of conduit 15 is constant at all points on any plane perpendicular to axial direction 5. Projection 9 creates a constricted region 4 (see FIG. 3) within conduit 15.

At the location of circumferentially-aligned jets 6, conduit 15 has an area A that, in the case of an annular conduit as shown in FIGS. 1-3, is calculated as $$A=\pi(R_o^2-R_i^2)$$

where $R_o$ is the distance of outer sidewall 2 from central axis $C_L$ and $R_i$ is the distance from central axis $C_L$ to the surface of insert 3 that forms the interior surface of conduit 15 at the position of jets 6.

Cross-sectional area A may be, for example, from 0.25 cm$^2$ to 120 cm$^2$.

Jets 6 have a hydrodynamic diameter indicated by $D_j$ in FIG. 3. In the case that the cross-sectional shape of jets 6 are not circular, the diameter is considered as the diameter of a circle have the same cross-sectional area of each jet 6. The diameter is that at the outlet of jets 6, i.e., at the point from which the organic polyamine is discharged into conduit 15. Jets 6 may not have a constant diameter along their length. In some embodiments, jets 6 are tapered, having a smallest diameter at their outlet.

The jet diameter $D_j$ may be, for example, at least 2 mm, at least 3 mm or at least 4 mm and may be, for example, up to 20 mm, up to 10 mm, up to 8 mm or up to 6 mm.

Constricted region 4 is defined as that portion of conduit 15, downstream of jets 6, having a cross-sectional area less than the cross-sectional area A of conduit 15. Thus, in FIG. 3, constricted region 4 begins at line 7, where projection 9 protrudes into conduit 15 and narrows it. Constricted region 4 in the embodiment shown in FIG. 3 reaches a minimum cross-sectional area at line 14. Constricted region 4 ends at line 8, where the cross-sectional area of conduit 15 again becomes equal to A. Downstream of the end of constricted region 4 (i.e., downstream of line 8) region 13 has a cross-sectional area as least as large as A and preferably larger than A (as shown in FIG. 3). Region 13 may form part of conduit 15 as shown in FIGS. 1-3, or may be or include another space in fluid communication with the outlet end of conduit 15.

The start of constricted region 4 (indicated as line 7 of FIG. 3) is between 0.01 and 3 jet diameters downstream of jets 6. This distance (indicated as $D_1$ in FIG. 3) is measured from the downstream edge of jets 6, which in FIG. 3 is indicated by line 12. In FIG. 3, this distance is approximately 0.25 jet diameters downstream of jets 6. "Downstream" for purposes of this invention indicates the direction of mass flow through conduit 15, which in FIGS. 1-3 is toward the right. "Upstream" refers to the opposite direction, which in FIGS. 1-3 is toward the left.

The end of constricted region 4 (indicated as line 8 of FIG. 3) is no more than 50 jet diameters downstream of jets 6. This distance (indicated as $D_2$ in FIG. 3) is measured from the downstream edge of jets 6, which in FIG. 3 is indicated by line 12. The end of constricted region 4 may be no more than 25, no more than 20, no more than 18, no more than 15, no more than 12, no more than 10 or no more than 8 jet diameters downstream of jets 6. In FIG. 3, the end of constricted region 4 is approximately 4 jet diameters downstream of jets 6.

As shown in FIG. 3, the cross-sectional area of constricted region 4 may not be constant along its length. In FIG. 3, the cross-sectional area of constriction region 4 reaches a minimum at line 14. The smallest cross-sectional area of constricted region 4 is at least 50% of cross-sectional area A and at most 85% of cross-sectional area A. It may be up to 75% of cross-sectional area A.

In embodiments in which the cross-sectional area of constricted region 4 is not constant along its length, the point at which the cross-sectional area of constricted region 4 first reaches its minimum is preferably 0.5 to 5, especially 1 to 3 jet diameters downstream from jets 6.

FIGS. 1-3 illustrate a preferred embodiment, in which the constricted region is produced by an circumferential projection 9 located on an internal surface of the outer sidewall 2 of conduit 15, perpendicular to the axially directed phosgene flow 5. It is possible, however, to produce the constriction by placing such an annular projection on the surface of insert 3 (i.e., the inner sidewall of an annular conduit of the type illustrated in FIGS. 1-3), or on both the inner and outer sidewalls of conduit 15).

In the embodiment shown in FIG. 3, annular projection 9 has a curved leading edge 11. The "leading edge" of the circumferential projection it that disposed toward the upstream end of conduit 15, i.e., facing the oncoming phosgene/organic amine flow.

As shown in FIG. 3, the organic polyamine injected into conduit 15 at each of jets 6 forms an organic polyamine stream. Because phosgene is simultaneously flowing through conduit 15, its momentum causes the organic polyamine stream to bend in a downstream direction, producing a curved flow path such as is indicated by reference numeral 10 of FIG. 3. In a preferred embodiment, the constricted region 4 is formed by an circumferential projection disposed on outer sidewall; the circumferential projection has a curved leading edge, and the curvature of the leading edge approximates the curved flow path of the organic polyamine stream, i.e., the curvature of leading edge 11 in FIG. 3 approximates that of curved flow path 10 of the organic polyamine stream. The leading edge may have a parabolic, elliptical, arc, or a hyperbolic curvature that aligns with the flow streamlines.

Downstream of constricted area 4, conduit 15 again widens to form a region 13 having a cross-sectional area at least as large as cross-sectional area A. As before, region 13 may be a separate apparatus rather than a portion of conduit 15, if desired. It is preferred that the cross-sectional area of region 13 is greater than cross-sectional area A. The cross-sectional area in region 13, if constant along its length, may be, for example, at least 1.5 times, at least 2 times, at least 3 times, at least 5 times or at least 10 times cross-sectional area A. As shown in FIG. 3, the cross-sectional area of region 13 may not be constant along its length. Thus, in some embodiments, the cross-sectional area of region 13 may increase along its length in the direction of mass flow, from A to at least 1.5 times, at least 2 times, at least 3 times, at least 5 times or at least 10 times cross-sectional area A. Region 13 may have any arbitrary length.

FIGS. 1-3 illustrate an embodiment of the invention in which conduit 15 has an annular cross-section. In other embodiments, conduit 15 has a circular cross-section. In other embodiments, conduit 15 could have an elliptical, rectangular or other regular polygonal, or oval cross-section.

In operation, an phosgene flow is established in conduit 15 upstream of jets 6, which flow travels sequentially past jets 6, through constricted region 4 and into region 13 of conduit 15. An organic polyamine is injected into conduit 15 through jets 6. The organic polyamine may be injected at right angles to the axially directed phosgene flow or at an angle thereto such as, for example, an angle of ±45° to ±89.9° thereto. At each jet, the injection of the organic polyamine produces an organic polyamine stream within the axially directed phosgene flow.

The organic polyamine stream is carried downstream by the axially directed phosgene flow and ultimately becomes mixed into it. Applicants have discovered, however, that prior to this invention, vaporization of phosgene, solvent and/or HCl formed in the phosgene/amine reaction occurs during the initial stages of mixing to form a mixture of gas and liquid phases. The gas phase can form near the boundary of the organic polyamine stream and the phosgene flow, inhibiting their mixing. The poorer mixing results in the formation of impurities and unwanted by-products. This formation of a gas phase and concomitant inhibition of mixing and impurity formation occurs within a very short time and distance after the organic polyamine is injected into the phosgene stream.

Although the invention is not limited by any theory, it is believed that by passing the phosgene flow and organic amine streams through the constricted area as described herein, vaporization is at least partially suppressed at a critical time for impurity and by-product formation. Suppressing vaporization reduces the volume of the gas phase formed during the initial stages of mixing, which in turn improves mixing of the phosgene with the organic polyamine, thereby reducing by-product and impurity formation. This beneficial effect is achieved with only a small increase in operating pressure due to the short length of the constricted region.

The flow rates of the axially directed phosgene flow and the injected organic polyamine stream preferably are such that the time for the mixed phosgene and organic polyamine streams to travel from jets 6 though constricted area 4 is no greater than 20 milliseconds.

The axially directed phosgene flow may contain phosgene by itself. Alternatively, the phosgene may be dissolved in a solvent that is liquid and unreactive under the conditions of the mixing and reaction steps that form the polyisocyanate in the process of the invention. The solvent should be a solvent for both phosgene and the organic polyamine. Suitable solvents include chlorinated aromatic hydrocarbons such as monochlorobenzene or dichlorobenzene, and non-halogenated aromatic hydrocarbons such as toluene. The solvent may constitute at least 50%, at least 75% or at least 80% and up to 95% or up to 90% of the total volume of the axially directed phosgene flow.

The organic polyamine stream includes at least one organic polyamine and optionally a solvent. The organic polyamine is characterized in having at least two primary amino groups.

The organic polyamine may be an aromatic polyamine in which the primary amino groups are bonded directly to a carbon atom of an aromatic ring. Examples of such aromatic polyamines include 2,4- and/or 2,6-toluene diamine (TDA), 4,4'-, 2,4'- and 2,2'-diphenyl methane diamine (MDA) or a mixture of any two or more thereof, various polymethylene polyphenyl amines (PMDA); mixtures of MDA and PMDA; naphthalene-1,5- or 1,8-diamine and the like.

The organic polyamine may be a cycloaliphatic polyamine such as hydrogenated MDA, 1-methyl-2,4-diaminocyclohexane, 1-methyl-2,6-diaminocyclohexane and the like.

The organic polyamine may be an aliphatic polyamine such as tetramethylene-1,4-diamine, hexamethylene-1,6-diamine, tetramethylxylylene diamine, trimethylhexane diamine, tetramethylhexane diamine, isophorone diamine, 1,3- and/or 1,4-bis(aminomethyl)cyclohexane and 2,4- or 2,6-diamine-1-methylecyclohexane.

A solvent, if present in the organic polyamine stream, may be as described with regard to the phosgene stream. The solvent may constitute at least 50%, at least 75% or at least 80% and up to 95% or up to 90% of the total volume of the organic polyamine stream.

The flow rates of the axially directed phosgene flow and the injected organic polyamine stream are such that the phosgene is in excess. The equivalent ratio of phosgene to primary amino groups provided to the reaction may be, for example, at least 1.5, and may be, for example, up to 15.

The phosgene and organic polyamine streams may be contacted at elevated temperature. The phosgene stream and organic polyamine stream each may be preheated, for example, to a temperature of 350 to 600° K and contacted with each other at such temperatures. Exothermic heat of reaction may result in a further temperature increase once the phosgene and organic polyamine streams have been combined.

The presence of the constricted area is believed to reduce or eliminate a stagnant region that tends to exist downstream of the jets 6 when the constricted area is not there. The stagnant region is an area where low downstream pressure can be communicated upstream, i.e., there is a direct path to a lower pressure downstream area.

The constriction blocks this communication, producing a higher pressure boundary condition just downstream of the organic amine jets as phosgene and organic polyamine streams pass through it, and thereby reducing or eliminated the unwanted vaporization. This in turn promotes better and faster mixing of the phosgene and organic polyamine, thereby reducing by-product and impurity formation.

Within any longitudinal plane within conduit 15 (including within constricted area 4) there exists a range of pressures that extends from a minimum pressure and a maximum pressure. That is to say, the pressure is not constant at all points in any such longitudinal plane, due at least in part to localized differences in velocities as the phosgene and organic polyamine streams begin to combine. There also exists within any such plane an average pressure, which is the mass-flow weighted average at all measured/predicted values on that axial plane).

The difference between the minimum pressure and average pressure is in general greatest at the location of jets 6 or immediately downstream thereof. As the reactor contents move downstream, the localized variation of pressure becomes smaller and the minimum and average pressures tend to move toward the same value. It is believed that the vaporization of volatile components tends to occur mainly in these areas of minimum pressure.

With this invention, the difference between the minimum pressure and average pressure is reduced in the region just downstream of jets 6, i.e., within the constricted region. This is accomplished because by passing the reactants through the constricted zone, the minimum pressures seen within the constricted area are increased, compared to the case in which the constricted area is absent (i.e., the cross-sectional area of conduit 15 downstream of jets remains equal to or greater than cross-sectional area A). The average pressure generally increases as well, but by a smaller amount, so the variation in pressure at any longitudinal plane within the restricted area is smaller. It is believed that the increase in minimum pressure reduces vaporization, which in turn promotes better and faster mixing of the phosgene and organic polyamine, thereby reducing by-product and impurity formation.

The minimum pressure within constricted region 4 may be increased by, of example, at least 0.25 atm (25 kPa), at least 0.5 atm (50 kPa), at least 1.0 atm (101 kPa) or at least 1.5 atm (152 kPa) to, for example, as much as 3 atm (304 kPa) or as much as 2.5 atm (253 kPa) within at least one longitudinal plane within constriction region 4, compared to the case in which the constricted region is absent. In a particular embodiment, the minimum pressure is at least 3 atm (304 kPa) gauge, at least 4 atm (405 kPa) or at least 4.5 atm (456 kPa) at all points within constricted region 4.

A small increase in average pressure is seen within the constricted area, compared to when the constricted area is not present. This increase in average pressure is typically of the order of 0.1 to 1.25 atmospheres (10.1 to 126.6 kPa) and is more typically up to about 1 atmosphere (101 kPa). In absolute terms, the pressure may reach a maximum of at least 5 atm (507 kPa) gauge, at least 8 atm (811 kPa), at least to 10 atm (1013 kPa), at least 13 atm (1317 kPa), at least 14 atm (1419 kPa) gauge, or at least 14.5 atm (1469 kPa), and may reach a maximum of up to 20 atm (2027 kPa), up to 18 atm (1824 kPa), up to 16 atm (1621 kPa), up to 15.5 atm (1570 kPa) or up to 15 atm (1520 kPa), within at least one longitudinal plane within constricted region 4.

Figure 4:
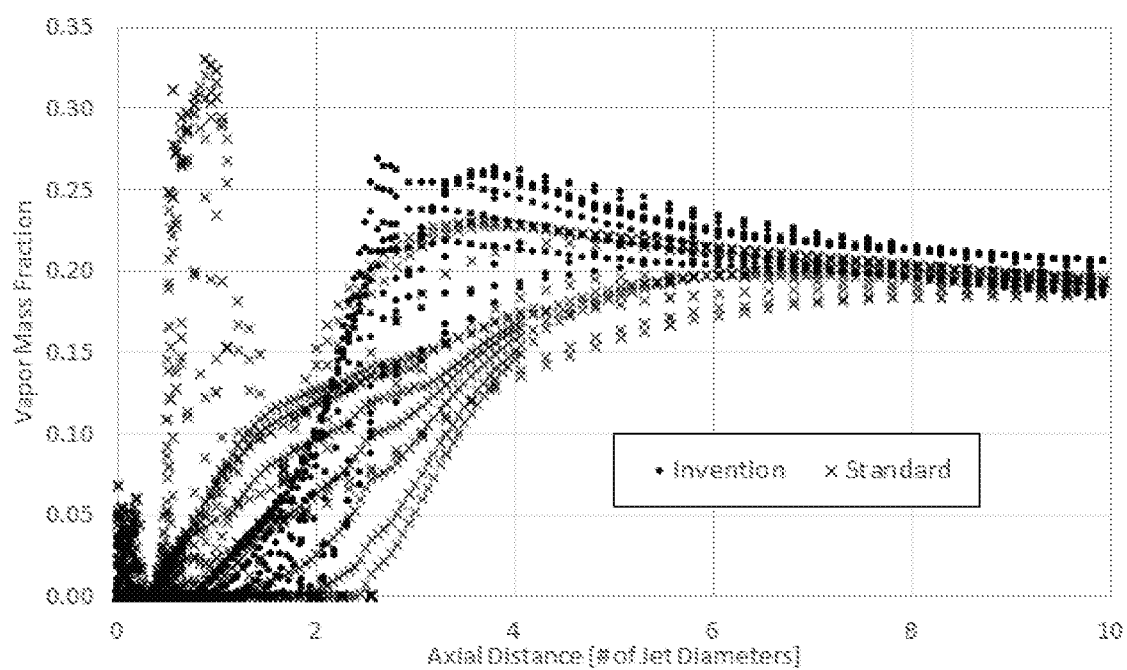
FIG. 4 is a graph comparing vapor mass fraction versus axial distance along the flow direction for comparative and inventive phosgenation methods.

A simulation is performed to compare the performance of a static mixing device as shown in FIGS. 1-3 with that described in FIGS. 3 and 4 of US Published Patent Application No. 2011-0230679. These mixers differ only in that the static mixer of the invention includes a constricted region 4 as shown in FIG. 3 hereof.

The simulations are performed using the following parameters:

Phosgene stream composition: 94% phosgene, 6% solvent.
Phosgene stream feed rate: 0.7 kg/s.
Phosgene stream temperature: 370° K.
Cross-sectional area A: 0.6 cm².
Jet diameter ($D_j$): 4 mm.
Organic polyamine stream composition: 28% diphenyl methane diamine, 72% solvent.
Organic polyamine stream feed rate: 0.6 kg/s.
Organic polyamine/solvent temperature: 440° K.
Minimum cross-sectional area of constricted region 4: 0.42 cm².

Once steady-state conditions are established, the minimum and average pressures are determined within constricted region 4 at various distances from jets 6. Results are as indicated in Table 1.

TABLE 1

| Axial Distance from Jets (# jet diameters) | Average Pressure, Atm (kPa) | | Minimum Pressure, Atm (kPa) | |
|---|---|---|---|---|
| | Without Constricted Region* | With Constricted Region | Without Constricted Region* | With Constricted Region |
| 0.5 | 14.0 | 14.8 | 2.7 | 4.7 |
| 0.8 | 13.2 | 14.0 | 3.4 | 5.5 |
| 1.0 | 12.6 | 13.5 | 4.1 | 6.1 |
| 1.3 | 12.0 | 12.9 | 5.2 | 6.4 |
| 1.5 | 11.7 | 12.4 | 6.0 | 6.8 |
| 1.8 | 11.4 | 11.9 | 6.4 | 7.2 |
| 2.1 | 11.1 | 11.6 | 6.6 | 7.5 |
| 2.3 | 10.9 | 11.3 | 6.7 | 7.6 |
| 2.6 | 10.7 | 11.0 | 6.9 | 7.8 |
| 2.8 | 10.4 | 10.6 | 7.0 | 8.0 |
| 3.1 | 10.2 | 10.5 | 7.1 | 8.0 |
| 3.3 | 10.1 | 10.4 | 7.2 | 8.1 |
| 3.6 | 10.0 | 10.3 | 7.3 | 8.2 |
| 4.1 | 9.9 | 10.1 | 7.5 | 8.1 |
| 5.1 | 9.6 | 9.8 | 7.7 | 8.1 |
| 7.7 | 9.3 | 9.4 | 7.8 | 8.3 |

*Not an example of this invention

The data in Table 1 illustrates the effect of the constricted region on average and minimum pressures.

Average pressure is somewhat high immediately downstream of jets 6 in both cases. As the data in Table 1 shows, the average pressure moderates somewhat in each case as one moves further downstream from jets 6. The effect of constricted area on average pressure is to increase it slightly, by as much as 0.8 to 1.0 atm (80 to 101 kPa) near the leading edge of constricted area 4. The increase in average pressure becomes smaller further downstream within constricted area 4.

As Table 1 further shows, there is a very large difference between the average and minimum pressures in areas slightly downstream of jets 6. At 0.5 jet diameters downstream, this difference, in the absence of constricted region 4, amounts to 11.3 atmospheres. The difference between average and minimum pressures decreases with increasing distance downstream from jets 6.

The presence of constricted region 4 increases the minimum pressures seen throughout that region, evidencing that "communication" with low pressure downstream areas is disrupted due to the presence of the constricted region. This effect is most pronounced in the upstream portions of constricted region 4, i.e., those regions closest to jets 6. At 0.5-1 jet diameters downstream from jets 6, the minimum pressure is increased by a full 2 atmospheres (102 kPa), or by as much as 75%.

The amount of vaporized material present within constricted region 4 is determined as a function of axial distance from jets 6, for both the inventive and comparative cases. The results are indicated graphically in FIG. 5.

In FIG. 4, the x markers indicate the vapor mass fraction (vapor mass divided by total mass) for the comparative case. The circular dots indicate the vapor mass fraction for the inventive case.

As can be seen in FIG. 5, a large vapor fraction develops immediately downstream of the jets in the comparative case (without constricted region 4). This large vapor fraction is not produced in the inventive case, in which constricted region 4 is present. FIG. 5 clearly shows the beneficial effect of constricted region 4 and the increased minimum pressures that are seen due to the presence of that region.

The amount of by-products generated is determined for each of the two simulations. By-products in the inventive case are reduced by 14% compared to the comparative case. The increased pressure drop needed to achieve this benefit is only 8%.

What is claimed is:

1. A method for mixing phosgene with an organic polyamine comprising;
    establishing an axially directed phosgene flow through a conduit having an outer sidewall;
    injecting the organic polyamine into the conduit through multiple circumferentially aligned jets, each such jet having a hydrodynamic diameter $D_j$ and each having a location on a wall of the conduit, to establish multiple organic polyamine streams into the axially directed phosgene flow; wherein the conduit has a cross-sectional area A at the location of the one or more jets;
    then passing the phosgene and the organic polyamine through a constricted region of the conduit that has a cross-sectional area less than A, wherein the constricted region is produced by a circumferential projection having a curved parabolic, elliptical, arc or hyperbolic leading edge that aligns with flow streamlines located on an internal surface of the outer sidewall of the conduit perpendicular to the axially directed phosgene flow and has a smallest cross-sectional area that is 50 to 95% of cross-sectional area A and wherein the constricted region begins downstream of the multiple jets at a distance equal to 0.01 to 3 times the hydrodynamic diameter $D_j$, reaches a minimum cross-sectional area at a distance equal to 1 to 3 times the hydrodynamic diameter Dj downstream of the multiple jets and extends downstream of the multiple jets to a distance that is no greater than 8 times the diameter hydrodynamic $D_j$; and
    thereafter passing the phosgene and the organic polyamine into a region having a cross-sectional area at least 2 times as large as cross-sectional area A.

2. The method of claim 1 wherein the conduit has an annular cross-section.

3. The method of claim 2 wherein the conduit has a cross-sectional width of 4 to 10 mm at the location of the jets and the jets each have a diameter of 3 to 7 mm.

4. A static mixing device comprising:
a) a conduit defined by an outer sidewall and optionally an inner sidewall, the conduit having a longitudinal axis, an inlet end for introducing a first fluid and an outlet end for removing a reaction product stream, the conduit defining a fluid flow path;
b) a plurality of circumferentially-aligned jets each having a location on a sidewall of the conduit between said inlet and outlet ends of the conduit, each jet providing a fluid flow path through the outer sidewall and into the conduit and each such jet having a hydraulic diameter $D_j$; wherein the conduit has a cross-sectional area A at the location of the jets;
c) a constricted region of the conduit, the constricted region being produced by a circumferential projection having a parabolic, elliptical, arc or hyperbolic leading edge that aligns with flow streamlines located on an internal surface of the outer sidewall of the conduit perpendicular to the axially directed phosgene flow and being further characterized in having a cross-sectional area less than A and being located downstream of the circumferentially-aligned jets and upstream of the outlet end of the conduit, wherein the constricted region has a smallest cross-sectional area that is 50 to 95% of cross-sectional area A and the constricted region begins downstream of the multiple jets at a distance equal to 0.01 to 3 times the diameter $D_j$, reaches a minimum cross-sectional area at a distance equal to 1 to 3 times the hydrodynamic diameter $D_j$ downstream of the multiple jets and extends downstream of the jets to a distance that is no greater than 8 times the diameter $D_j$; and
d) a region, downstream of and in fluid communication with the constricted region of the conduit, which has a cross-sectional area of at least 2 times A.

* * * * *